(12) United States Patent
Betz (10) Patent No.: US 7,270,001 B2
(45) Date of Patent: Sep. 18, 2007

(54) ULTRASONIC MEASUREMENT OF THE RUNNING TIME AND QUANTITY FOR DETECTING THE CONCENTRATION OF PARTICLES IN A FLOWING FLUID

(75) Inventor: Oliver Betz, Gröbenzell (DE)

(73) Assignee: Systec Controls Mess und Regeltechnik GmbH, Puchheim (DE)

( * ) Notice: Subject to any disclaimer, the term of this patent is extended or adjusted under 35 U.S.C. 154(b) by 0 days.

(21) Appl. No.: 10/516,030

(22) PCT Filed: May 31, 2003

(86) PCT No.: PCT/DE03/01783

§ 371 (c)(1),
(2), (4) Date: Jun. 22, 2005

(87) PCT Pub. No.: WO03/102512

PCT Pub. Date: Dec. 11, 2003

(65) Prior Publication Data

US 2006/0005611 A1    Jan. 12, 2006

(30) Foreign Application Priority Data

May 31, 2002   (DE) ................................ 102 24 294

(51) Int. Cl.
*G01F 23/00* (2006.01)
(52) U.S. Cl. .................................. 73/290 V; 73/290 R
(58) Field of Classification Search ............... 73/61.75, 73/290 V, 290 R
See application file for complete search history.

(56) References Cited

U.S. PATENT DOCUMENTS

| 3,575,050 A | | 4/1971 | Lynnworth |
| 3,731,532 A | | 5/1973 | Courty |
| 3,779,070 A | * | 12/1973 | Cushman et al. .......... 73/865.5 |
| 4,718,269 A | | 1/1988 | Der Kinderen |
| 5,125,514 A | | 6/1992 | Oehler et al. |
| 5,533,408 A | | 7/1996 | Oldenziel et al. |
| 6,481,268 B1 | * | 11/2002 | Povey et al. ............... 73/61.75 |

(Continued)

FOREIGN PATENT DOCUMENTS

GB       2 156 075        10/1985

(Continued)

*Primary Examiner*—Hezron Williams
*Assistant Examiner*—Rodney Frank
(74) *Attorney, Agent, or Firm*—Volpe and Koenig, P.C.

(57) ABSTRACT

A method for ultrasonic measurement of the running time and quantity of a flowing fluid is provided, in which the running time of an ultrasonic signal (70) is measured counter to and in a direction of the flow (5), wherefrom the flow rate of the fluid is determined. Reflections of the ultrasonic signal (70) from particles in the fluid are also detected in order to determine a concentration of particles. A device for carrying out the method includes two ultrasonic transducers which can be switched from a transmission mode to a reception mode. The ultrasonic transducers in the transmission mode transmit ultrasonic signals that are received by the ultrasonic transducers in the reception mode once the signal (70) has penetrated the fluid to be analyzed. At least one of the ultrasonic transducerscan be switched from the transmission mode to the reception mode so that it can receive reflections (E1, E2, E3) of its transmitted signal. Additional transducers can be provided that also receive the reflections.

8 Claims, 8 Drawing Sheets

U.S. PATENT DOCUMENTS

| | | | |
|---|---|---|---|
| 6,698,276 B2 * | 3/2004 | Povey et al. | 73/61.75 |
| 6,698,277 B2 * | 3/2004 | Povey et al. | 73/61.75 |
| 6,748,815 B2 * | 6/2004 | Povey et al. | 73/865.5 |
| 6,796,195 B2 * | 9/2004 | Povey et al. | 73/865.5 |

FOREIGN PATENT DOCUMENTS

| | | |
|---|---|---|
| JP | 61 288 185 | 12/1986 |
| JP | 2000 321104 | 11/2000 |

* cited by examiner

Fig. 6 though additional ultrasonic transducers are designed that
ULTRASONIC MEASUREMENT OF THE RUNNING TIME AND QUANTITY FOR DETECTING THE CONCENTRATION OF PARTICLES IN A FLOWING FLUID

BACKGROUND

The invention is directed to a method for the ultrasonic measurement of the running time and quantity of a flowing fluid, in which the running time of an ultrasonic signal is measured counter to and in the direction of the flow, wherefrom the flow rate of the fluid is determined. In addition, the invention concerns a device for carrying out such a method.

Figure 1:
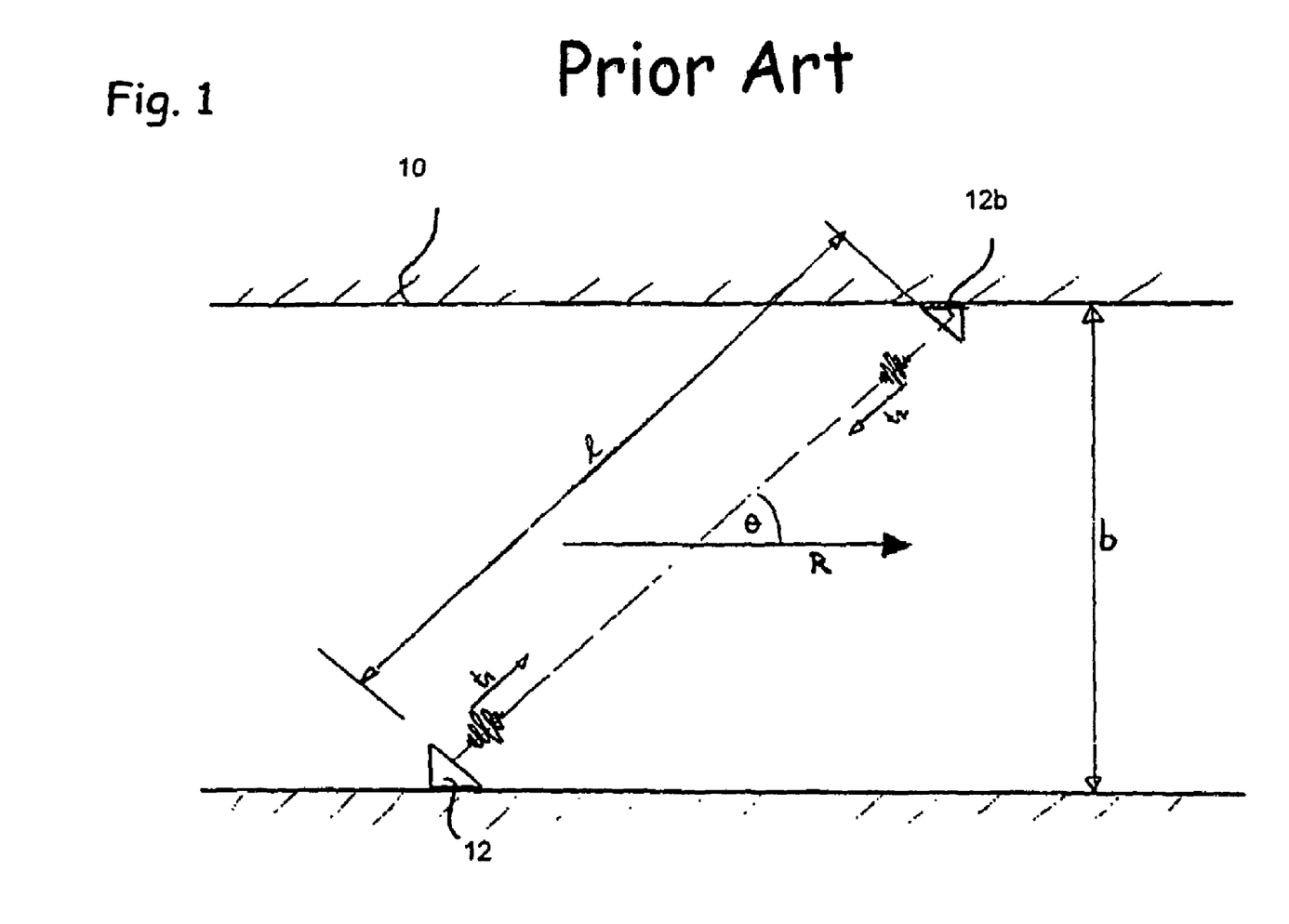
FIG. 1 a schematic view of a device for carrying out a running time method according to the state of the art.

The ultrasonic running time method is a known and proven method for the determination of the flow rate of fluids such as fluid or gaseous media in pipes or ducts. For an ultrasonic running time method according to the state of the art (FIG. 1), at least two ultrasonic transducers $12a$, $12b$ are arranged staggered towards the direction of flow R in a flow-through measurement cross section 10. The distance 1 between the two ultrasonic transducers $12a$, $12b$ is greater than the width b of the flow-through measurement cross section. In this respect, the ultrasonic transducers $12a$, $12b$ can be both wetted by a medium as well as attached from the outside to the wall of the measurement cross section 10. By means of the inherent speed of the medium, ultrasonic signals that are sent diagonally with the flow downstream require a lower running time $t_1$ than the ultrasonic signal that is sent upstream (running time $t_2$). If the distance between the ultrasonic transducers as well as the angle θ between ultrasonic path and direction of flow are known, then the average flow rate can be determined from the difference in running times $dt=t_2-t_1$:

$$v = \frac{l}{2\cos\theta} \cdot \frac{dt}{t_1 \cdot t_2}$$

Figure 2:
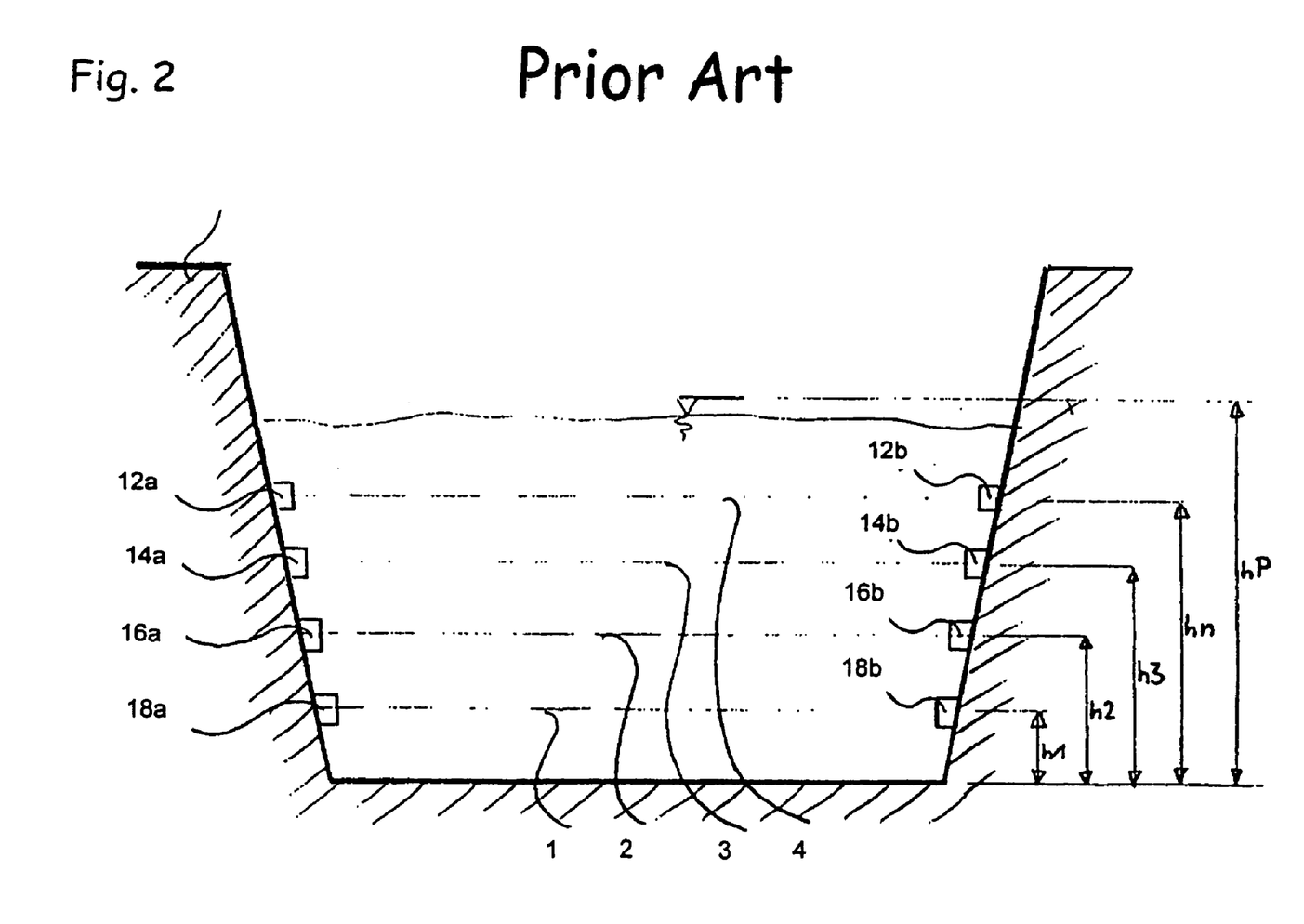
FIG. 2 a cross-section through the device from FIG. 1 along the line II-II in FIG. 1.
Figure 3:
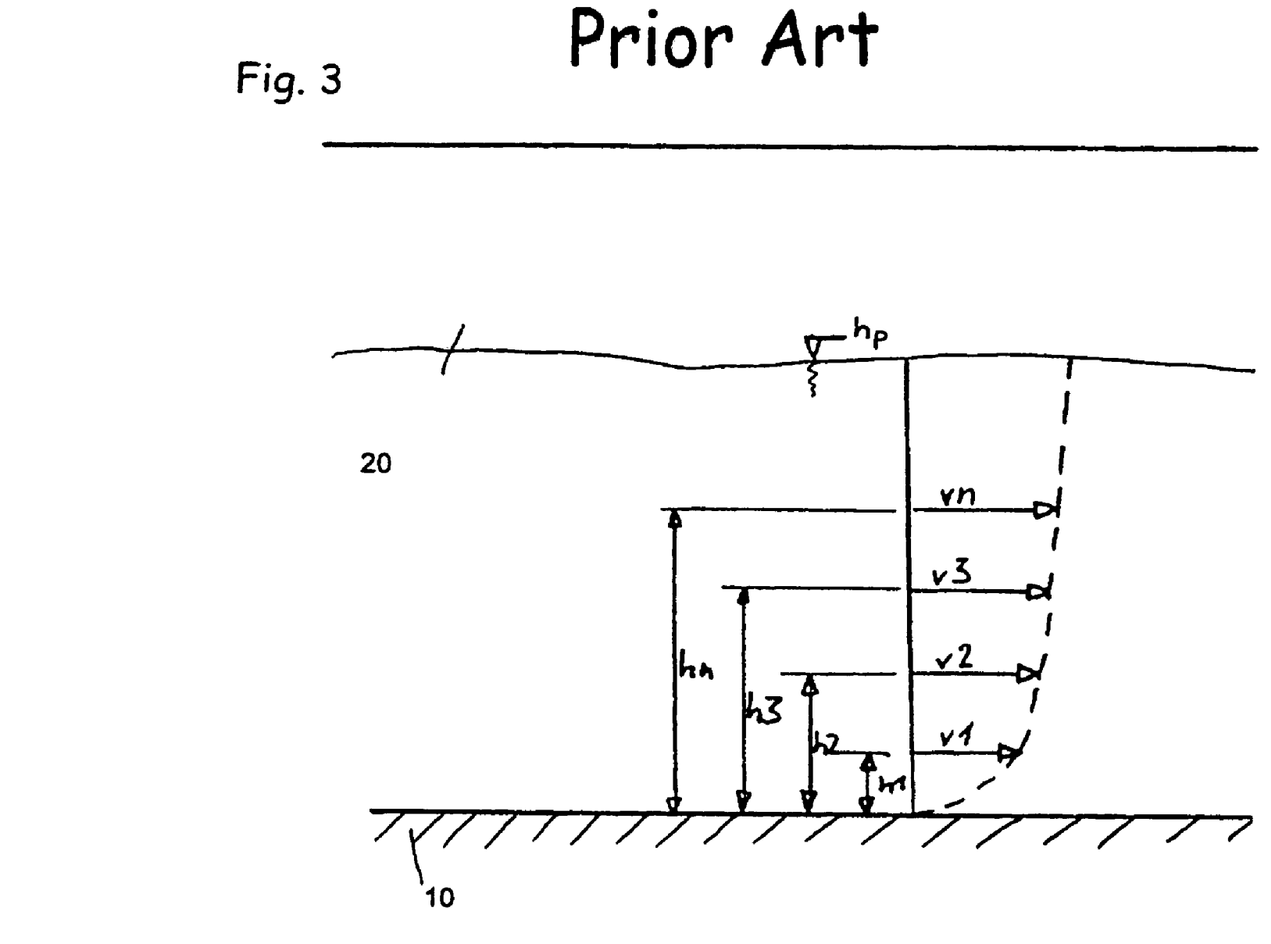
FIG. 3 a schematic illustration of a flow rate profile that can be determined with a device according to FIGS. 1 and 2.

To determine the difference in running times, in modern measurement devices the received signals are digitized and then analyzed with an analysis computer (Digital Signal Processor, DSP). Multiple-path ultrasonic flow-through measurements are used because of the complex flow conditions for flow-through measurement in large cross-sections and for flow-through measurement for free-flow cross-sections. As an example, FIG. 2 shows one such flow-through measurement in a measurement cross-section 10 in the form of an open channel in which a fluid 20 with a liquid level $h_p$ flows. In this example, horizontal measurement paths 1 through n are arranged on top of each other between ultrasonic transducers $12a$, $12b$, $14a$, $14b$, $16a$, $16b$, $18a$, $18b$ arranged in pairs such that the unequal speed distribution $v_1$ through $v_n$ over the height of the liquid levels $h_1$ through $h_n$ (FIG. 3) can be determined. By means of a suitable integration, the average flow rate in the cross-section can thus be calculated with high accuracy. Such measurement methods are described in the ISO/DIS 6416, for example.

For many applications for which the ultrasonic flow-through analyzer comes into use, the measurement of the particle density or diffusion would be of great interest alongside the measurement of the amount of flow-through. As examples are mentioned here the measurement of flue- and exhaust gases, the measurement of air-flow streams for combustion control, the measurement behind filters and the measurement of inflows and outflows in waste water treatment plants. In the mentioned examples, the measurement of particles is partially specified in order to fulfill environmental requirements, for example, and/or it is an important parameter in order to optimally monitor or control the processes.

There are processes for the measurement of the concentration of particles according to known optical principles. In doing so the attenuation of a light by means of scattering and absorption is used for the calculation of the concentration of the particles in the fluid. However, these methods monitor a very small control volume that is assumed to be representative for the entire measurement cross-section. In addition, these methods provide no locally-resolved measurement value. A further disadvantage is that these methods are susceptible to contamination and thus maintenance-intensive, for example, against the buildup of algae or the deposit of suspended matter on the light sources or sensors.

SUMMARY

The objective of the invention is to create a method for the measurement of the amount of flow-through with ultrasound, which offers an inexpensive and reliable possibility for the measurement of the concentration of particles.

To this end the reflection of the ultrasonic signal by particles in the fluid is also detected by a method of the kind initially mentioned in order to thus determine the concentration of the particles. In terms of a method for the measurement of the amount of flow-through, no additional ultrasonic transducers are necessary to detect the reflections. The method according to the invention can thus be carried out inexpensively with a measurement device for the measurement of the amount of flow-through that is already available. Compared to known methods for the measurement of the concentration of particles, the method according to the invention is more reliable because the ultrasonic transducers are less susceptible to contamination than optical sensors.

According to a second aspect, the object of the invention is also solved by means of a device for the implementation of the method mentioned above with at least two ultrasonic transducers that are switchable from a transmission mode to a reception mode, whereby the ultrasonic transducers in the transmission mode can send ultrasonic signals that can be received by the ultrasonic transducers in the reception mode, after they have crossed the fluid flow to be analyzed, and whereby at least one of the ultrasonic transducers can be switched so quickly from transmission to reception that it can receive the reflection of its own sent signal. Therefore, no separate sensor is necessary for the receipt of reflections so that the device can be manufactured inexpensively; that is to say, a measurement device for the measurement of the amount of flow-through that is already available can be used without installation expense or can be converted.

According to another aspect, the problem is solved by means of a device for the implementation of the method mentioned above with at least two ultrasonic transducers which can be switched from the transmission mode to a reception mode, whereby the ultrasonic transducers in the transmission mode can send ultrasonic signals that can be received by ultrasonic transducers in the reception mode, after they have crossed the fluid flow to be analyzed, and whereby additional ultrasonic transducers are designed that are arranged such that the reflection of the signal sent from the ultrasonic transducer in the transmission mode can be received. Thus, specially-matched ultrasonic transducers are designed for the receipt of the reflections.

Additional embodiments of the invention are provided in the dependent claims.

BRIEF DESCRIPTION OF THE DRAWINGS

The invention will be described in detail based on the preferred embodiments which follow. For this purpose, reference is made to the attached drawings in which.

DETAILED DESCRIPTION OF THE PREFERRED EMBODIMENTS

Figure 4:
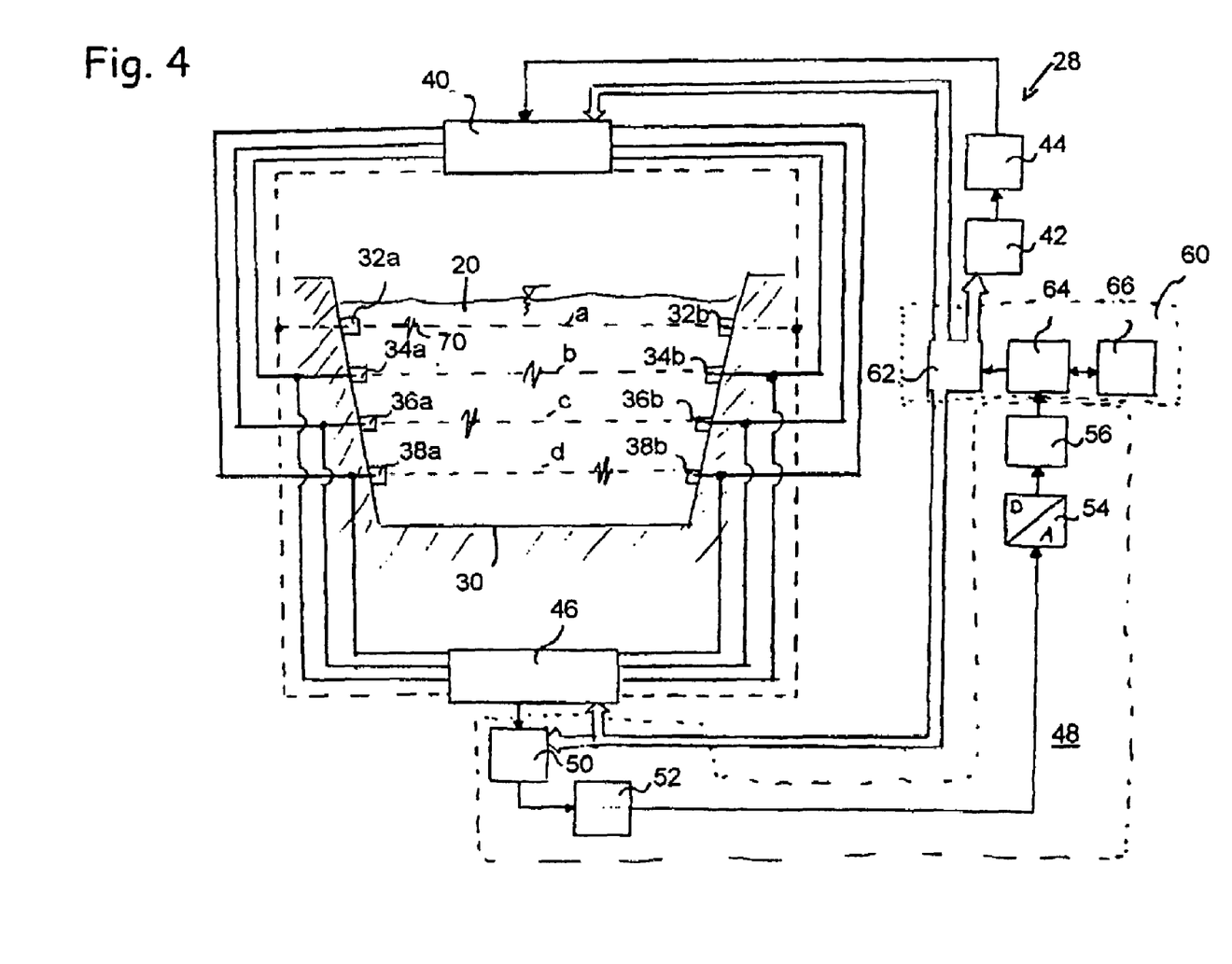
FIG. 4 a schematic illustration of a device according to an embodiment of the invention.

A preferred embodiment of a device 28 according to the invention is illustrated in FIG. 4.

Figure 5:
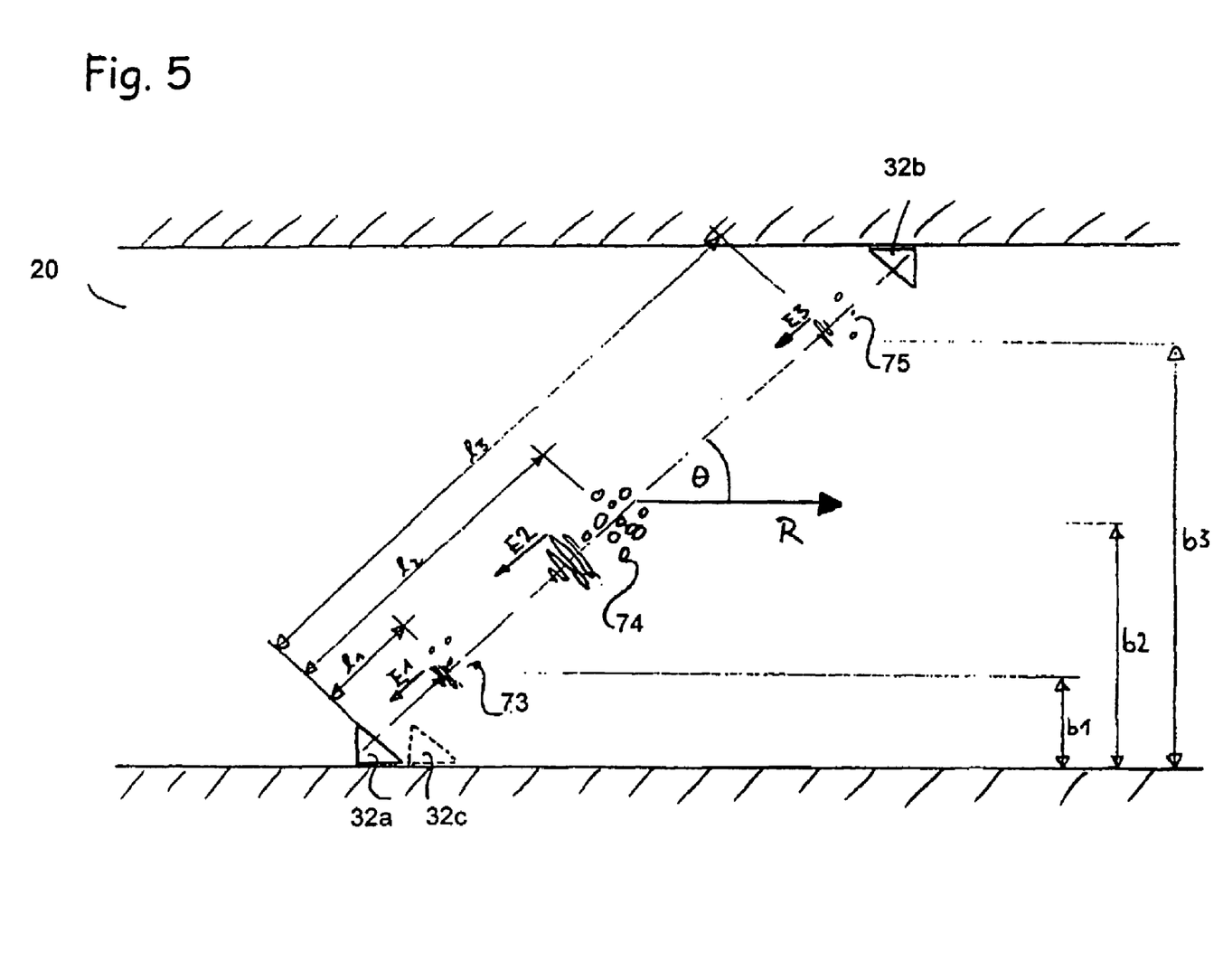
FIG. 5 a schematic illustration of a mode of operation of the device from FIG. 4.

Multiple ultrasonic transducers 32a, 32b, 34a, 34b, 36a, 36b, 38a, 38b are installed in pairs in the cross section of an open channel 30 to be measured such that paths a, b, c, d in each case span between the members of one of the pairs of transducers 32a and 32b, 34a and 34b, 36a and 36b, 38a and 38b that the cross-section of the channel 30 crosses from one side wall to the other at different depths. The paths a, b, c, d include an angle θ with the direction of flow R of the fluid 20 (see also FIG. 5), whereby the paths can be passed through in a direction with the flow and in an opposite direction against the flow of fluid 20. The ultrasonic transducers 32a, 32b, 34a, 34b, 36a, 36b, 38a, 38b are connected over a transmission multiplexer 40 with a signal generator 42 with amplifier 44 and over a reception multiplexer 46 with a signal processing device 48 such that each of the ultrasonic transducers 32a, 32b, 34a, 34b, 36a, 36b, 38a, 38b can be switched to a transmitter or receiver. The signal processing device 48 includes a filter 50, an amplifier 52, an analog/digital transducer 54 in which the filtered and amplified signals are digitized from the ultrasonic transducers, and a memory 56, in which the digitized signals are saved for further analysis.

A control and analysis device 60 contains a fast sequence control system 62 that controls the signal generator 42, the transmission multiplexer 40 and the reception multiplexer 46, a calculating device with processor 64 for the analysis of the signals retained in the memory 56, and an operating- and monitoring device 66 for the operation of the measurement device 28 and for information output.

Figure 6:
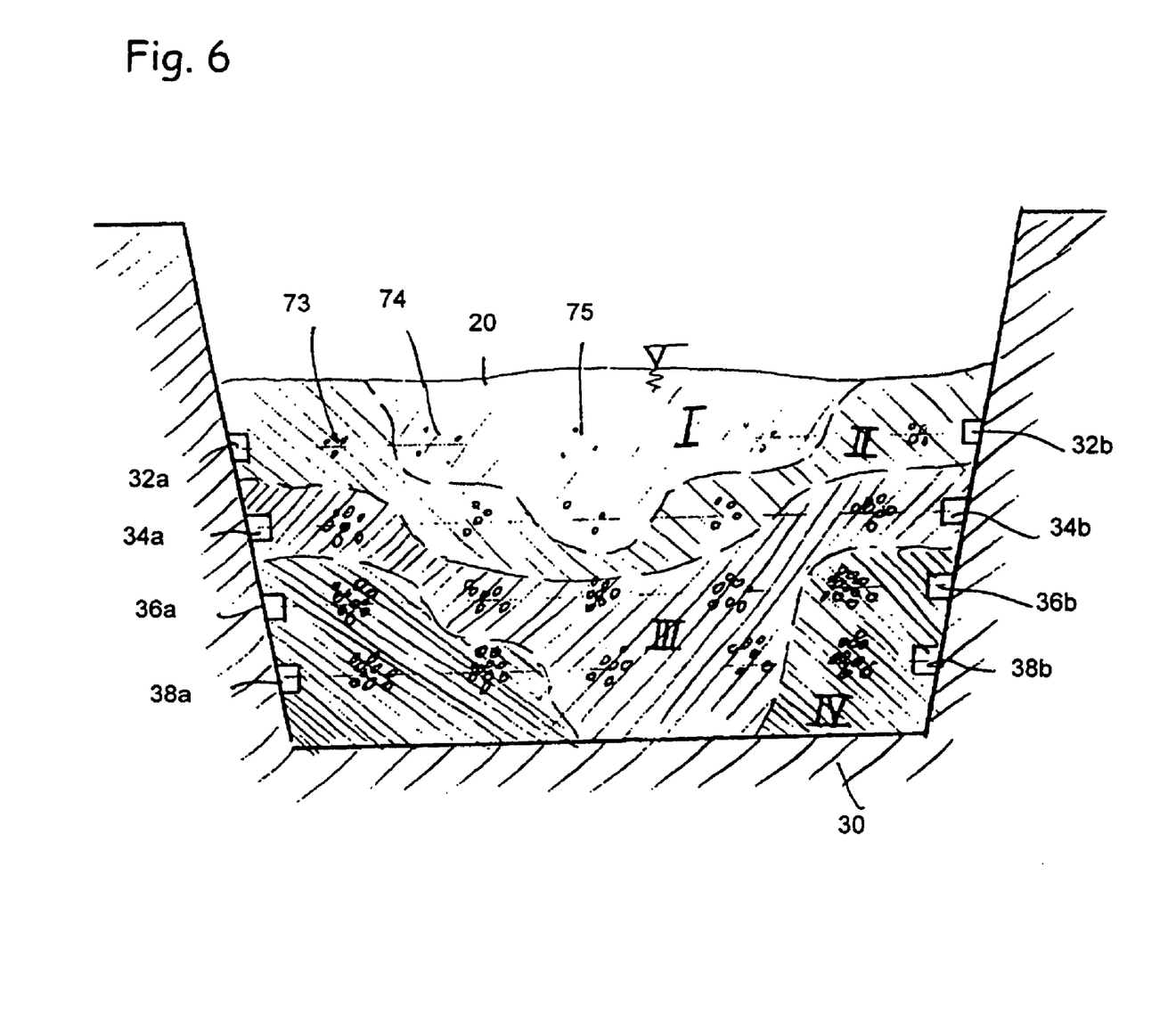
FIG. 6 a schematic illustration of the local distribution of the concentration of particles such as can be determined with the method according to the invention.

For the measurement of the flow rate of the fluid 20, for example for the determination of the amount of flow-through, in each case one ultrasonic transducer of 32a and 32b, 34a and 34b, 36a and 36b, 38a and 38b is switched in the known ways to a transmitter, and the other as a receiver respectively. In order to avoid crosstalk between the different paths a through d, only one of the respective ultrasonic transducers is switched to a transmitter at the same time. By way of example, if the ultrasonic transducer 32a is switched to a transmitter, it is stimulated by means of a short electrical signal from the signal generator 42, such as is illustrated by way of example in FIG. 6, and sends out an ultrasonic signal 70 that spreads out along the path a to receiver 32b and is registered there such that the running time $t_1$ of the signal can be determined. Subsequently, the ultrasonic transducer 32b is switched to a transmitter and an ultrasonic signal 70 is sent in the opposite direction of the path a, which requires a running time $t_2$. From the difference of running times $t_1$ and $t_2$, the flow rate can be calculated in known ways.

However, the ultrasonic signal 70 is also reflected by the particles 73, 74, 75 contained in the fluid 20. The reflected ultrasonic signals E1, E2, E3 are shifted in their frequency (Doppler effect) by means of the proper motion of particles 73, 74, 75. In order to be able to evaluate the reflections E1, E2, E2 of the ultrasonic signal 70 so that the concentration of the particles 73, 74, 75 in the cross-section can be calculated, the ultrasonic transducers 32a or 32b that are switched to a transmitter are switched to a receiver immediately after transmitting the ultrasonic signal 70. With this it can receive the reflections E1, E2, E3 and transmit over the reception multiplexer 46 to the signal processing device 48 for analysis.

Figure 7:
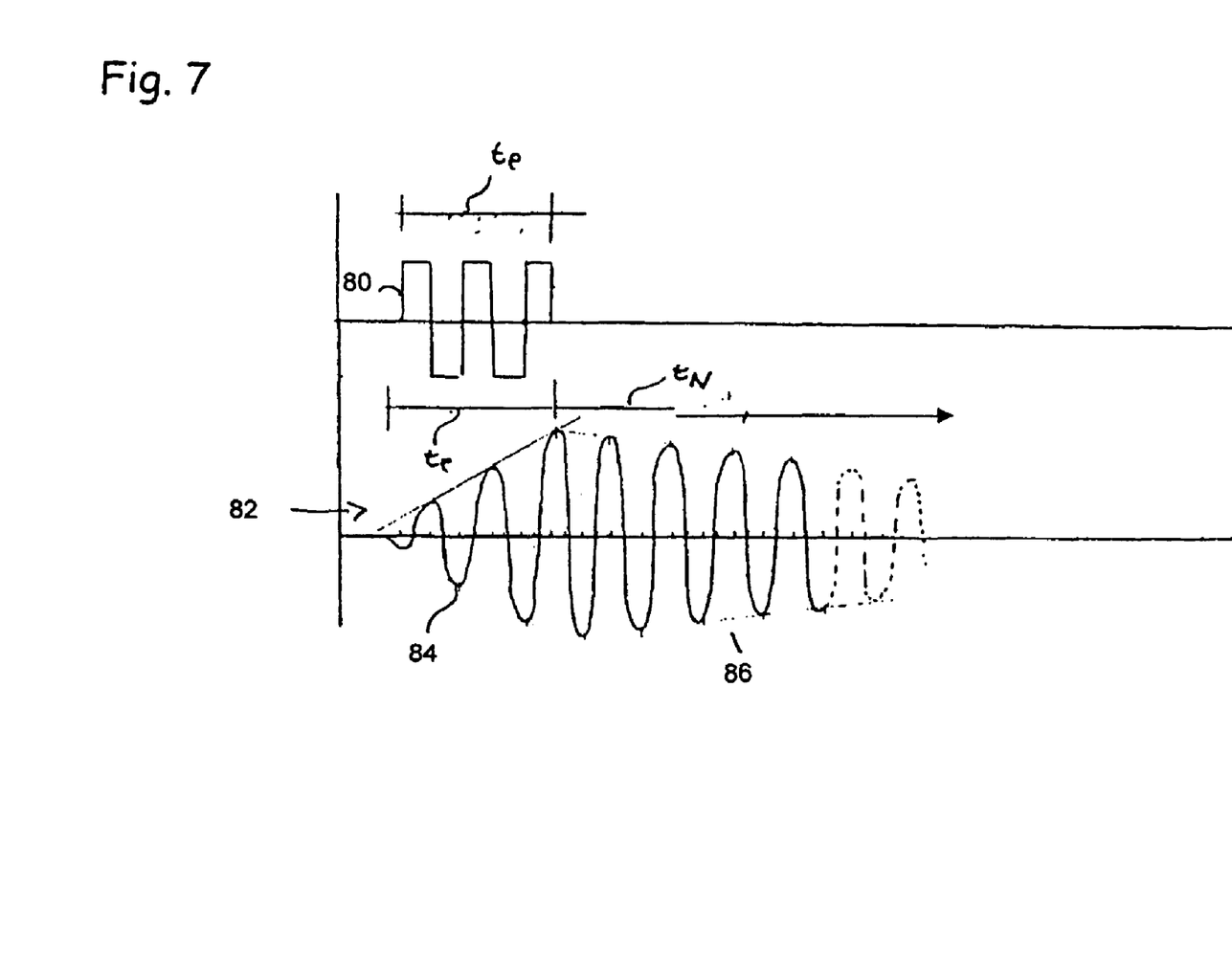
FIG. 7 a schematic illustration of the temporal progression of an initial stimulus signal for an ultrasonic transducer and the wave reply of the transducer to this signal.

Should the same ultrasonic transducer function as a receiver shortly after transmitting, the natural frequency of the ultrasonic transducer must be quickly absorbed. It is known that ultrasonic transducers possess a time of reverberation $t_N$. In order that it can quickly be received again, a brief time of reverberation $t_N$ is desirable. If the ultrasonic transducer is stimulated by means of a simple pulse signal 80 for the length $t_e$ as illustrated in FIG. 7, then the natural frequency of the ultrasonic transducer reacts similarly to the illustrated curve 82. A reverberation phase 86 with a long time of reverberation $t_N$ follows upon a natural frequency phase 84.

Figure 8:
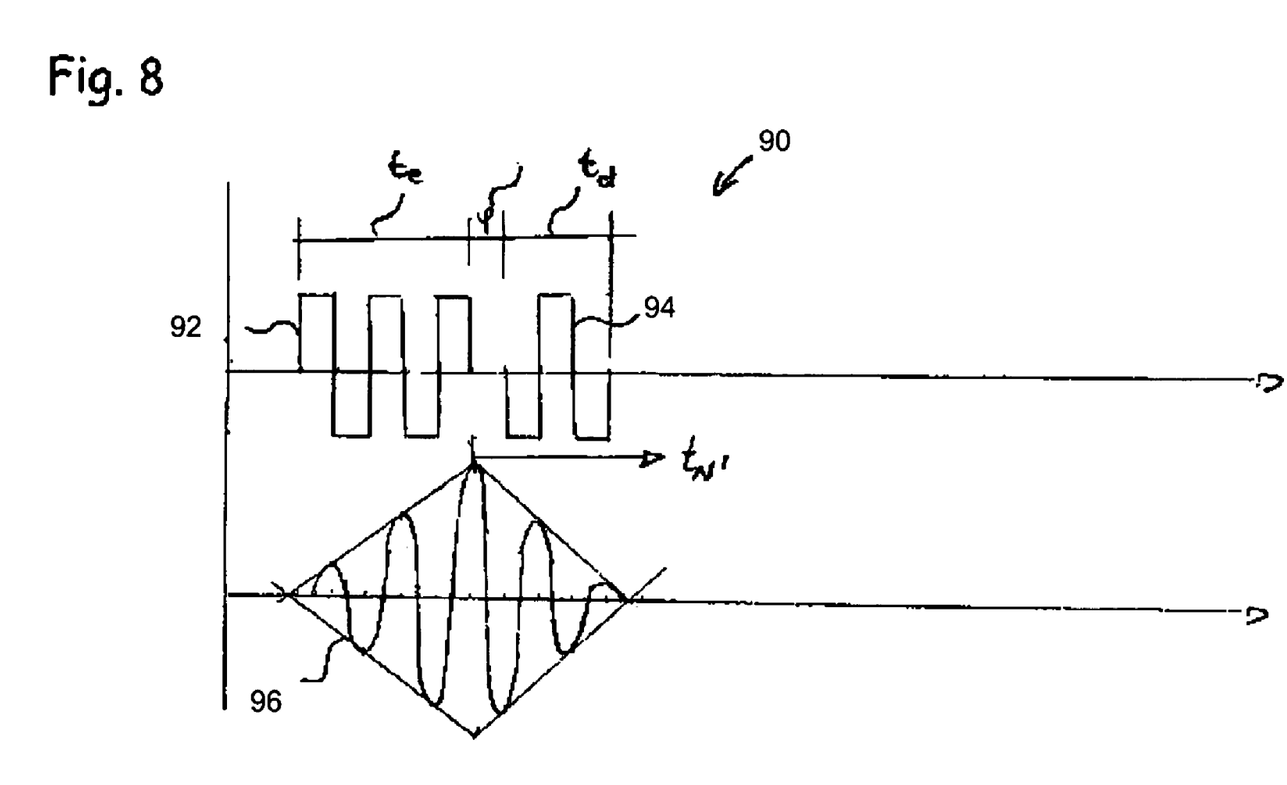
FIG. 8 a schematic illustration of the temporal progression of a second stimulus signal for an ultrasonic transducer and the wave reply of the transducer to this signal.

A long time of reverberation $t_N$ can be avoided at one of the ultrasonic transducers by means of a constructive configuration. The time of reverberation $t_N$ can also be appreciably shortened, however, by means of a sensible configuration of the transmission signal from the signal generator 42. A transmission signal is illustrated in FIG. 8, by which a phase shift φ is included after a stimulus part 92 of length $t_e$, after which an absorption part 94 of length $t_d$ follows. If the phase shift φ is selected such that the absorption part 94 counteracts the waves 96 of the ultrasonic transducer, then a clearly shortened time of reverberation $t_N^1$ can be achieved. Consequently, the ultrasonic transducer can be used substantially more quickly as a receiver.

After the digitization of the reflected signals in the A/D transducer 54, the concentration of particles can be determined by means of an amplitude analysis. By means of a temporal discretization of the reflected signals E1, E2, E3, the elimination of the reflection waves 73, 74, 75 from the transmitter—in FIG. 5 ultrasonic transducer 32a—can be determined. For this purpose the sonic speed $v_S$ of the medium must first be determined. According to FIG. 1, this results from the path length 1 divided by the average running time 0.5 $(t_1+t_2)$. The elimination $l(t)$ of the particles on which the reflection $E(t)$ arose, is thus the result of $$l(t) = 0,5 \frac{vS}{t}$$

By means of the detection of the reflections E1, E2, E3 at multiple paths a through d, locally dissolved particle densities can be illustrated (FIG. 6) as well as accurate averages from the complete measurement cross-section determined by means of suitable algorithms.

By means of the described method, the operator has a substantially higher resolution of the measurement cross-section and for this reason a higher accuracy of the measurement results than for the selective measurement of the particle density according to the state of the art.

It is particularly advantageous if the detection of the reflections for measurement of the concentration of particles is carried out with the available ultrasonic transducers. Then neither additional installation expense is necessary nor do further device costs accrue.

Before the digitization in the A/D transducer 54, the detected reflections are filtered in a filter 50. The filter 50 is constructed such that only the double-shifted reflections remain unabsorbed. The filter parameters are preferably changeable by the sequence control system 62.

Thus the range of bandwidth of the filter 50 can be matched to the Doppler shift to be expected from the reflections in reliance on the measured flow rate of the fluid 20.

Advantageously, not only can reflections be detected on the path on which they were sent. Reflections and base signals in particular can be detected by means of the receivers arranged on the other paths and be pulled up for analysis. In this manner the waves of the reflections and base signals can be resolved locally in great detail and the concentration distribution of the particles accurately determined with it.

In addition to the ultrasonic transducers 32a, 32b, 34a, 34b, 36a, 36b, 38a, 38b designed for the measurement of the amount of ultrasonic running time, according to another implementation form of the invention additional, separate ultrasonic transducers 32c (FIG. 5) can be designed for the detection of the reflections E1, E2, E3. Either of the reflections E1, E2, E3 can then be detected with these separate ultrasonic transducers 32c such that a higher local resolution of the concentration of particles is possible. By means of a suitable configuration of the receiver, a spatial resolution of the concentration of particles is also possible.

Or, instead of the transducers 32a, 32b, 34a, 34b, 36a, 36b, 38a, 38b, only the separate ultrasonic transducers are used for the detection of the reflections. This offers the opportunity to use specially-designed transducers that are particularly matched to their function, the reception. The ultrasonic transducers 32a, 32b, 34a, 34b, 36a, 36b, 38a, 38b that should function as transmitters for the measurement of the amount of running time, as a rule posses a minor radiation angle at which the vectored signal is given off, and also for this reason a mostly small reception angle. In contrast, it is advantageous for the detection of the radiated signal if the receiver possesses a large reception angle.

The invention claimed is:

1. Method for the ultrasonic measurement of the running time of flowing fluid, comprising measuring the running time of an ultrasonic signal (70) counter to and in a direction of flow (R), determining a flow rate of the fluid therefrom; and detecting reflections of the ultrasonic signal (70) by particles in the fluid in order to determine a concentration of the particles,
wherein an electrical transmission signal (90) is used for creation of the ultrasonic signal (70) in an ultrasonic transducer (32a, 32b, 34a, 34b, 36a, 36b, 38a, 38b) that includes a stimulus part (92) and an absorption part (94).

2. Method according to claim 1, wherein the concentration of the particles is determined by an amplitude analysis of the reflections of the ultrasonic signal (70).

3. Method according to claim 1, wherein a local concentration distribution (73, 74, 75) of the particles is determined by analysis of the running time of the reflections (E1, E2, E3) of the ultrasonic signal (70).

4. Method according to claim 3, wherein a flow rate profile is determined by analysis of the running time of several ultrasonic signals along several paths and the local concentration distribution of the particles is determined by analysis of the reflections of several ultrasonic signals.

5. Method according to claim 1, wherein the absorption part (94) exhibits a phase shift ($\phi$) compared to the stimulus part (92) such that a reverberation of the ultrasonic transducer is counteracted.

6. Method according to claim 1, wherein the detected reflections (E1, E2, E3) are narrow-band filtered before analysis.

7. Device for detecting concentrations of particles in a flowing fluid according to claim 1, comprising at least two ultrasonic transducers (32a, 32b, 34a, 34b, 36a, 36b, 38a, 38b) that are switchable from a transmission mode to a reception mode so that the ultrasonic transducers can send out ultrasonic signals (70) in the transmission mode that can be received from the ultrasonic transducers after they have crossed the fluid flow (20) to be analyzed, wherein at least one of the ultrasonic transducers (32a, 32b, 34a, 34b, 36a, 36b, 38a, 38b) is switchable from a transmission mode to a reception mode so that it can receive reflections (E1, E2, E3) of the signal (70) it sent out itself.

8. Device for detecting concentrations of particles in a flowing fluid according to claim 1, comprising at least two ultrasonic transducers (32a, 32b, 34a, 34b, 36a, 36b, 38a, 38b) that are switchable from a transmission mode to a reception mode, whereby the ultrasonic transducers can send out ultrasonic signals (70) in the transmission mode that can be received by the ultrasonic transducers in the reception mode after they have crossed the fluid flow (20) to be analyzed, wherein additional ultrasonic transducers (32c) are arranged to receive reflections (E1, E2, E3) of the signals (70) sent out by the ultrasonic transducers in the transmission mode.

* * * * *